United States Patent
Liu et al.

(10) Patent No.: US 12,239,515 B2
(45) Date of Patent: Mar. 4, 2025

(54) THREE DIMENSIONAL NONWOVEN AND ABSORBENT ARTICLES HAVING THE SAME

(71) Applicant: The Procter & Gamble Company, Cincinnati, OH (US)

(72) Inventors: Zhe Liu, Beijing (CN); Songmei Zhou, Beijing (CN); Meng Wang, Beijing (CN); Qi Yang, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 634 days.

(21) Appl. No.: 17/202,608

(22) Filed: Mar. 16, 2021

(65) Prior Publication Data
US 2022/0249304 A1    Aug. 11, 2022

Related U.S. Application Data

(63) Continuation of application No. PCT/CN2021/075475, filed on Feb. 5, 2021.

(51) Int. Cl.
*A61F 13/514*    (2006.01)
(52) U.S. Cl.
CPC .. *A61F 13/51476* (2013.01); *A61F 13/51401* (2013.01); *A61F 13/5146* (2013.01); *A61F 13/51496* (2013.01); *A61F 2013/51452* (2013.01)
(58) Field of Classification Search
CPC .......... A61F 2013/51452; A61F 13/513; A61F 13/51104; A61F 13/51108
See application file for complete search history.

(56) References Cited

U.S. PATENT DOCUMENTS

| | | |
|---|---|---|
| 9,322,119 B2 | 4/2016 | Erdem |
| 9,463,606 B2 | 10/2016 | Okuda et al. |
| 9,844,476 B2 | 12/2017 | Hammons et al. |
| 10,758,431 B2 | 9/2020 | Splendiani |
| 11,214,893 B2 | 1/2022 | Ashraf et al. |
| 11,896,466 B2 | 2/2024 | Giovanni |
| 2006/0243367 A1 | 11/2006 | Engelhart et al. |

(Continued)

FOREIGN PATENT DOCUMENTS

| | | |
|---|---|---|
| CN | 103908370 A | 7/2014 |
| CN | 109562005 A | 4/2019 |

(Continued)

OTHER PUBLICATIONS

All Office Actions, U.S. Appl. No. 17/227,449.
(Continued)

*Primary Examiner* — Susan S Su
*Assistant Examiner* — Katherine-Ph Minh Pham
(74) *Attorney, Agent, or Firm* — Christian M. Best

(57) ABSTRACT

The present disclosure relates to a three dimensional nonwoven comprising a protruded area comprising a first area having a first light reflectance and a second area having a second light reflectance. The three dimensional nonwoven comprises a recess comprising a third area having a third light reflectance, wherein the first light reflectance is different from the second light reflectance, as measured according to Light Reflectance Test. The present disclosure also related to an absorbent article comprising the three dimensional nonwoven.

21 Claims, 9 Drawing Sheets

(56) References Cited

U.S. PATENT DOCUMENTS

| | | | |
|---|---|---|---|
| 2008/0108962 A1 | 5/2008 | Furuta et al. | |
| 2012/0282436 A1* | 11/2012 | Coe | B29C 59/04 |
| | | | 264/156 |
| 2016/0235590 A1 | 8/2016 | Coe et al. | |
| 2017/0056256 A1* | 3/2017 | Smith | A61F 13/515 |
| 2017/0258645 A1* | 9/2017 | Orr | A61F 13/538 |
| 2017/0258649 A1* | 9/2017 | Rosati | A61F 13/5116 |
| 2018/0228656 A1 | 8/2018 | Schneider et al. | |
| 2018/0344537 A1 | 12/2018 | Kurihara | |
| 2019/0117472 A1 | 4/2019 | Erdem et al. | |
| 2022/0080105 A1 | 3/2022 | Askem et al. | |

FOREIGN PATENT DOCUMENTS

| | | | |
|---|---|---|---|
| CN | 305578140 | 1/2020 | |
| CN | 305578140 S | 1/2020 | |
| CN | 305578141 | 1/2020 | |
| CN | 305578141 S | 1/2020 | |
| JP | 2009240589 A | 10/2009 | |
| WO | WO-2018079302 A1 * | 5/2018 | ............. A61F 13/49 |
| WO | 2019076287 A1 | 4/2019 | |

OTHER PUBLICATIONS

U.S. Appl. No. 17/227,449, filed on Apr. 12, 2021, to Rosati Rodrigo et al.
PCT Search Report and Written Opinion for PCT/CN2021/075475 dated Jul. 30, 2021, 12 pages.

* cited by examiner

THREE DIMENSIONAL NONWOVEN AND ABSORBENT ARTICLES HAVING THE SAME

CROSS REFERENCE TO RELATED APPLICATION

This application is a continuation, under 35 U.S.C. § 120, of Application No. PCT/CN2021/075475, filed on Feb. 5, 2021, which is herein incorporated by reference in its entirety.

FIELD

The present disclosure relates to a three dimensional nonwoven and an absorbent article comprising the same.

BACKGROUND

Nonwovens including synthetic fibers formed from thermoplastic resin are widely used as sheets constituting absorbent articles such as sanitary napkins, infant disposable diapers, personal care disposable diapers, and the like.

These absorbent articles comprise several layers providing different functions. A liquid permeable topsheet is disposed closest to the wearer's skin and should be capable of quickly absorbing the excreted fluid. A backsheet is disposed on the opposed, garment-facing side of the article. Some absorbent articles in the market further comprises a nonwoven outermost layer forming at least part of a garment-facing surface of an absorbent article. Other components of absorbent articles are well known, and include in particular an absorbent core disposed between the topsheet and the backsheet to absorb and retain the excreted fluids.

Three dimensional nonwovens comprising three dimensional elements can provide craftsmanship perception as well as functional improvements. Three dimensional nonwovens may also provide improved fluid handling properties, and improved sensory feels such as skin softness, and cushion feel, etc.

As one effort to enhance three-dimension impression, a height of protrusions providing a three dimensional profile to a three dimensional nonwoven may be increased. However, such an approach is not satisfactory. Nonwovens are often relatively tightly wound on the rolls and stored and transported to an absorbent article manufacturing location. The associated high winding pressures may compress nonwoven and result in a reduced nonwoven caliper, and the nonwoven may lose a visual three dimensional appearance. In addition, a high protrusion structure may significantly lower material modulus. During absorbent article production process where nonwovens are unwound from the rolls and supplied to a production line that converts the nonwoven into a component of absorbent articles, nonwoven are stretched. When stretched, a nonwoven with a low modulus tends to more easily cause undesired wrinkles which deteriorate visual appearance of the absorbent article.

Meanwhile, an absorbent article having a three dimensional nonwoven topsheet and/or a three dimensional outermost layer has been desirable as it can provide craftsmanship perception and delightful impression.

There is a continuous need for a cost effective nonwoven which can create well perceivable three dimensional appearance, and for an absorbent article having such a nonwoven.

SUMMARY

The present disclosure provides a three dimensional nonwoven comprising a protruded area comprising a first area having a first light reflectance and a second area having a second light reflectance, and a recess comprising a third area having a third light reflectance, wherein the first light reflectance is different from the second light reflectance, as measured according to Light Reflectance Test.

The present disclosure also provides an absorbent article comprising a skin-facing surface, a garment-facing surface, a liquid permeable topsheet, a liquid impermeable backsheet, an absorbent structure disposed between the topsheet and the backsheet, and a three dimensional nonwoven of the present disclosure.

For ease of discussion, the three dimensional nonwoven and the absorbent article will be discussed with reference to the numerals referred to in figures. The figures and detailed description should however not be considered limiting the scope of the claims, unless explicitly indicated otherwise, and the invention disclosed herein is also used in a wide variety of absorbent article forms.

DETAILED DESCRIPTION

All ranges are inclusive and combinable. The number of significant digits conveys neither limitations on the indicated amounts nor on the accuracy of the measurements. All numerical amounts are understood to be modified by the word "about" unless otherwise specifically indicated.

The term "absorbent articles", as used herein, include disposable diapers, sanitary napkins, panty liners, incontinence pads, interlabial pads, breast-milk pads, sweat sheets, animal-use excreta handling articles, animal-use diapers, and the like.

The term "component" of an absorbent article, as used herein, refers to an individual constituent of an absorbent article, such as a topsheet, secondary layer, acquisition layer, liquid handling layer, absorbent core or layers of absorbent cores, backsheet, and outer cover.

Three Dimensional Nonwoven

As used herein, the term "nonwoven" or "nonwoven" refers to a web having a structure of individual fibers or threads which are interlaid, but not in a repeating pattern as in a woven or knitted fabric, which do not typically have randomly oriented fibers. Nonwoven or fabrics have been formed from many processes, such as, for example, meltblowing, spunbonding, hydroentangling, airlaid, wetlaid, through-air-dried paper making processes, and bonded carded web processes, including carded thermal bonding. The nonwoven can comprise unbonded fibers, entangled fibers, tow fibers, or the like. Fibers can be extensible and/or elastic, and may be pre-stretched for processing. Fibers can be continuous, such as those produced by spunbonded methods, or cut to length, such as those typically utilized in a carded process. Fibers can be bicomponent, multiconstituent, shaped, crimped, or in any other formulation or configuration known in the art for nonwoven and fibers. In general, the fibers can be bondable, either by chemical bond (e.g. by latex or adhesive bonding), pressure bonding, or thermal bonding. If thermal bonding techniques are used in the bonding process described below, a certain percentage of thermoplastic material, such as thermoplastic powder or fibers can be used.

Figure 1:
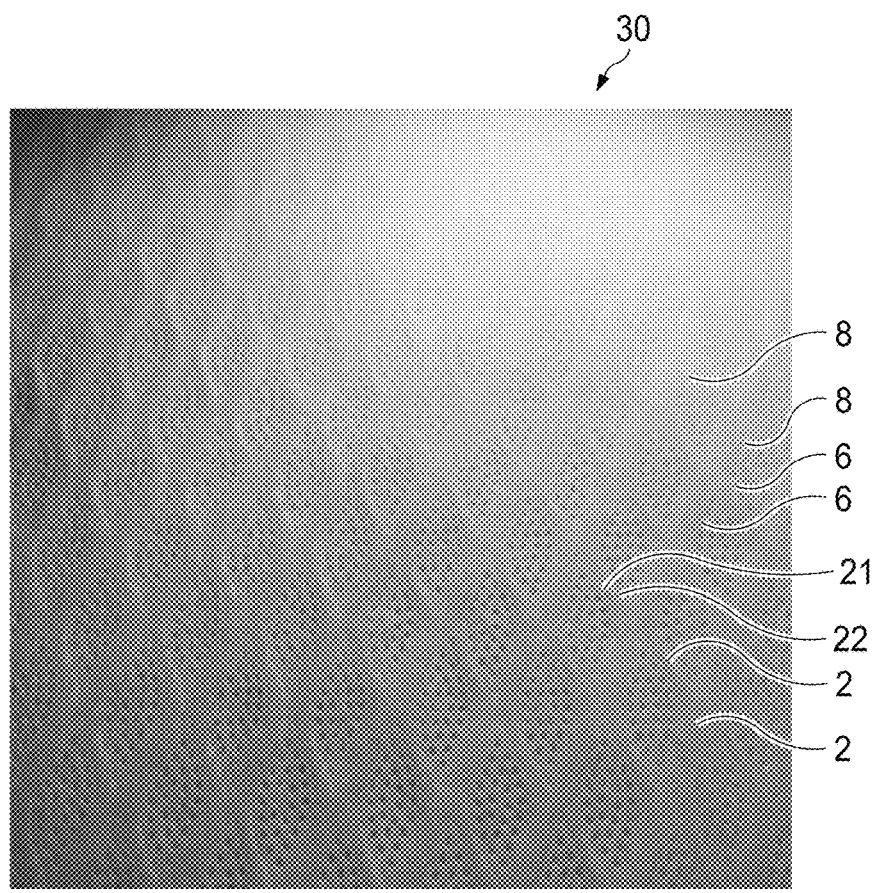
FIG. 1 is a plan view of a nonwoven according to the present disclosure.
Figure 2:
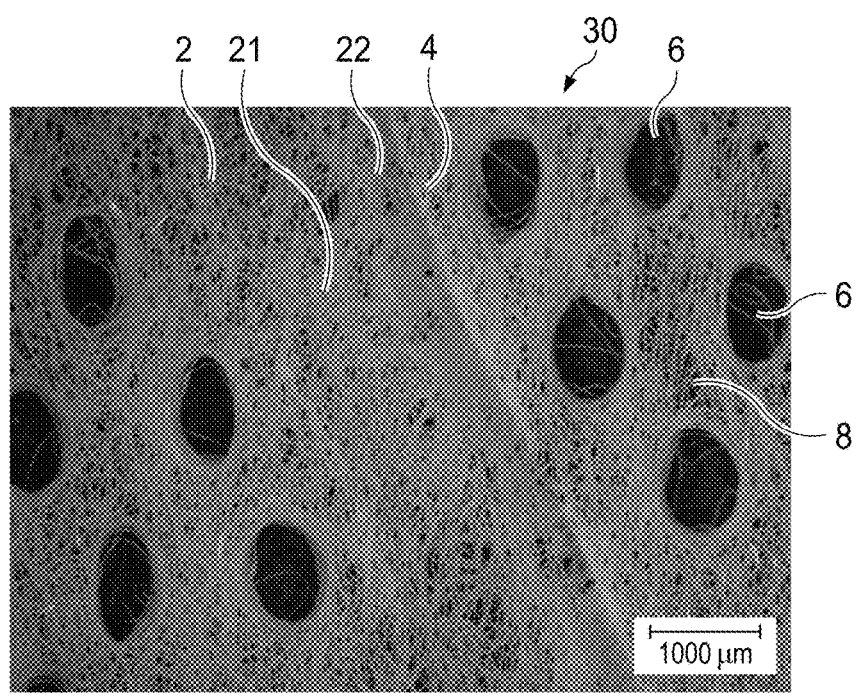
FIG. 2 is a magnified plan view of part of the nonwoven of FIG. 1.
Figure 3:
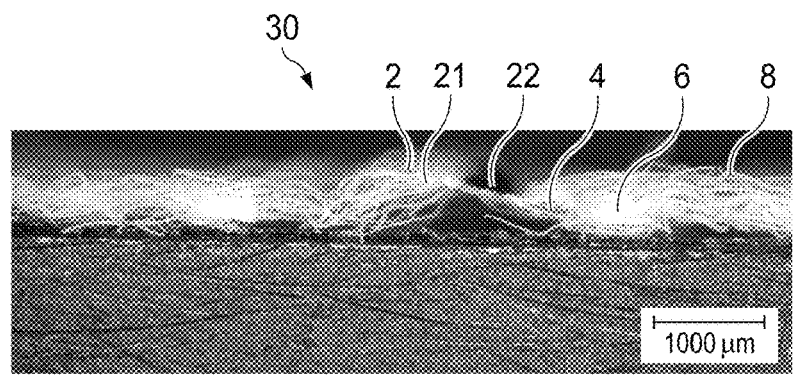
FIG. 3 is a partial cross-section view of the nonwoven of FIG. 1.

The present disclosure provides a three dimensional nonwoven suitable for a component such as a topsheet and an outer cover, an outermost sheet, of an absorbent article. FIGS. 1 and 2 show a plan view of a three dimensional nonwoven of the present disclosure and a magnified plan view thereof, respectively. FIG. 3 shows a partial cross-section view of the nonwoven of FIG. 1. Referring to FIGS. 1-3, a three dimensional nonwoven 30 of the present disclosure comprises at least one protruded area 2 which comprises a first area 21 having a first light reflectance and a second area 22 having a second light reflectance which is different from the first light reflectance.

The three dimensional nonwoven 30 further comprises at least one recess 8 comprising a third area 4, the third area 4 being adjacent to the second area 22. In one embodiment, the second area 22 is located along at least a part of a periphery of the recess 8. The three dimensional nonwoven 30 may comprise a plurality of recesses 8, as shown in FIG. 1. The recess 8 may be substantially surrounded by the protruded area 2. The term "substantially surrounded" herein intends to mean that at least 80% of a periphery of the recess is surrounded by the protruded area. In one embodiment, the three dimensional nonwoven 30 comprises a plurality of recesses 8, each recess 8 being surrounded by the protruded area 2 as shown in FIG. 1. In another embodiment, the three dimensional nonwoven 30 comprises a plurality of protruded areas 2, each protruded area 2 being surrounded by the recess 8.

The third area 4 may have a third light reflectance and a third thickness.

In some embodiments, the three dimensional nonwoven of the present disclosure is a carded nonwoven such as a carded air-through nonwoven.

The three dimensional nonwoven of the present disclosure may comprise one or more layers.

In some embodiments, the three dimensional nonwoven comprises at least two layers each of which remains as a discrete layer which may be attached to each other by, for example, thermal bonding, compression, adhesive bonding or any combination thereof. The first layer and the second layer in the nonwoven may be bonded to each other without using chemicals such as adhesive and latex.

In some embodiments, the three dimensional nonwoven comprises a unitary structure. A unitary structure herein intends to mean that although it may be formed by several sub-layers that have distinct properties and/or compositions from one another, they are somehow intermixed at the boundary region, so that, instead of a definite boundary between sub-layers, it would be possible to identify a region where the different sub-layers transition one into the other. Such a unitary structure is typically built by forming the various sub-layers one on top of the other in a continuous manner, for example using air laid or wet laid deposition. Typically, there is no adhesive used between the sub-layers of the unitary material. However, in some cases, adhesives and/or binders can be present although typically in a lower amount that in multilayer materials formed by separate layers.

The three dimensional nonwoven may comprise thermoplastic fibers. The nonwoven may comprise any suitable types of thermoplastic fibers, such as polypropylene fibers, other polyolefins, other polyesters besides PET such as polylactic acid, thermoplastic starch-containing sustainable resins, other sustainable resins, bio-PE, bio-PP, and Bio-PET. The nonwoven may comprise any other suitable types of fibers such as viscose fibers, rayon fibers, or other suitable nonwoven fibers, for example. These fibers may have any suitable deniers or denier ranges and/or fiber lengths or fiber length ranges. The three dimensional nonwoven may comprise bicomponent fibers. Bicomponent fibers can have a sheath and a core. The sheath and the core may also comprise any other suitable materials known to those of skill in the art. The core/sheath composite fibers may comprise a core component comprising a resin and a sheath component comprising a thermoplastic resin having a melting point of at least about 20° C. lower than a melting point of the resin of the core component. The sheath and the core may each comprise about 50% of the fibers by weight of the fibers, although other variations (e.g., sheath 60%, core 40%; sheath 30%, core 70% etc.) are also within the scope of the present disclosure. The bicomponent fibers or other fibers that make up the first and/or second layers may have a denier in the range of about 0.5 to about 6, about 0.75 to about 4, about 1.0 to about 4, about 1.5 to about 4, about 1.5 to about 3, about 1.5 to about 2.5, or about 2, specifically including all 0.1 denier increments within the specified ranges and all ranges formed therein or thereby. Denier is defined as the mass in grams per 9000 meters of a fiber length. In other instances, the denier of the fibers of the first layer may be in the range of about 1.5 denier to about 6 denier or about 2 denier to about 4 denier and the denier of the fibers of the second layer may be in the range of about 1.2 denier to about 3 denier or about 1.5 denier to about 3 denier, specifically reciting all 0.1 denier increments within the specified ranges and all ranges formed therein or thereby. Bicomponent fibers can be a side-by-side type fibers.

In a form, the basis weight of the three dimensional nonwoven may be appropriately selected depending on the nonwoven application. For the nonwoven of the present disclosure as a topsheet or an outer cover of an absorbent article, a basis weight of the nonwoven may be from about 15 gsm (g/m$^2$) to about 75 gsm, or from about 20 gsm to about 75 gsm, or from about 30 gsm to about 65 gsm. All other suitable basis weight ranges for the nonwoven are within the scope of the present disclosure. Accordingly, the basis weight of the nonwoven may be designed for specific product requirements.

Protruded Area

Referring to FIGS. 1-3, the three dimensional nonwoven 30 comprises at least one protruded area 2 providing a three dimensional profile to the nonwoven 30. The protruded area 2 comprises a first area 21 having a first light reflectance and a second area 22 having a second light reflectance which is different from the first light reflectance. The difference between the first light reflectance and the second light reflectance may be no less than about 6, no less than about 8, or no less than about 10, as measured according to Light Reflectance Test. In one embodiment, the second light reflectance is greater than the first light reflectance. The second light reflectance may be no less than about 100, or no less than about 105 or no less about 108, as measured according to Light Reflectance Test. Without wishing to be bound by theory, the protruded area 2 has a first area 21 and a second area 22 which have different light reflectances, so that light reflectance contrast between the first area 21 and the second area 22 enhances visual perception of three dimensional structure of the nonwoven.

In one embodiment, the second area 22 is a highly heat-fused in such a way that the second area 22 is heat-fused in a higher extent than the first area 21 in the protruded area 2. When the second area 22 is highly heat fused, the second area 22 has a light reflectance higher than the first area 21 as the second area 22 has a less pore area where no fiber exists than the first area 21 in a unit area.

Referring to FIGS. 1 and 3, the second area 22 may be located on a wall of protruded area 2. When the second area 22 is located on the wall of the protruded area it can increase a contrast effect between the first area 21 and the second area 22 with little or no impact on the nonwoven softness. The second area 22 may be located only on a wall of protruded area 2, and is not located on a top of the protruded area 22.

The protruded area 2 may be continuous extending in one or more directions in the three dimensional nonwoven 30, as shown in FIG. 1. In one embodiment, the protruded area 2 may be continuous extending in one direction, for example substantially along a machine direction, a length direction of the nonwoven. In another embodiment, the three dimensional nonwoven of the present disclosure comprises a plurality of discrete protruded areas 22.

The second area 22 may be formed along at least part of a periphery of protruded area 2. The second area 22 may be formed along at least part of a periphery of the protruded area 2 in a length direction of the protruded area 2 in such a way that the length of the second area 22 is shorter than the length of the protruded area 2, referring to FIG. 1. The term "length direction" in this context intends to mean a direction along which the protruded area extends. The protruded area 2 may have the second area 22 along the entire periphery of protruded area 2.

The first area 21 has a first thickness and the second area 22 has a second thickness different from the first thickness. The second thickness may be no greater than about 100 μm, or no greater than about 80 μm, as measured according to Thickness Test. The first thickness may be no less than about 500 μm, or no less than 600 μm, as measured according to Thickness Test.

The second area may have a length no less than about 3 mm, no less than about 4 mm, or no less than 5 mm, measured according to Light Reflectance Test. The second area may have an area no less than about 2 mm$^2$, or no less than about 2.5 mm$^2$, measured according to Light Reflectance Test.

The protruded area may form a pattern. A pattern formed by the protruded area may be any shape of pattern, for example, a shape of one or multiple linear lines or curved lines, a circles, an ellipse, a triangle, a polygon, a flower, a cloud, and the like. The pattern may be a regular, homogeneous and uniform pattern or an irregular, non-uniform and non-homogeneous pattern. In some embodiments, nonwoven of the present disclosure comprises a plurality of protruded areas, wherein the protruded areas are not necessarily in the same shape or size. That is, one protruded area may differ from another protruded area in the nonwoven of the present disclosure. Patterns may be various shapes and/or various sizes. The nonwoven of the present disclosure may have uniform protruded patterns.

The protruded area may coordinate with graphics, indicia, printing, inks, color, and/or patterned adhesives, for example, located in the nonwoven or in another component of an absorbent article when it is used as a component of an absorbent article.

Recess

Referring to FIGS. 1-3, the three dimensional nonwoven 30 further comprises at least one recess 8 comprising a third area 4, the third area 4 being adjacent to the second area 22. A recess herein intends to mean an area having a lower height than the protruded area including a land area which is not concaved, and a concaved area.

The third area 4 has a third light reflectance. The third light reflectance may be different from the second light reflectance of the second area 22. The difference between the second light reflectance and the third light reflectance may be no less than about 6, no less than about 8, or no less than about 10, as measured according to Light Reflectance Test. In one embodiment, the second light reflectance is greater than the third light reflectance.

The recess 8 may comprise a plurality of elements which may comprise apertures, embosses or a combination thereof. In one embodiment, the recess 8 comprises a plurality of apertures as shown in FIGS. 1-3.

The elements may be in any of circular, oval, hour-glass shaped, star shaped, polygonal and the like, and combinations thereof. Polygonal shapes include, but are not limited to triangular, quadrilateral, hexagonal, octagonal or trapezoidal. In one embodiment, elements are circular. In another embodiment, elements are an oval shape. Elements may have a size in a range of about 0.1 mm$^2$-about 3 mm$^2$, or in a range of about 0.2 mm$^2$-about 2 mm$^2$, or in a range of about 0.3 mm$^2$-about 1 mm$^2$. The recess may have elements having the same size and/or shape. The recess may have elements having different sizes and/or shapes.

The recess may form a pattern. Descriptions of a pattern stated with respect to protruded area, supra are applicable to the pattern formed by the recess.

Nonwoven Manufacturing Process

The three dimensional nonwoven of the present disclosure may be made by any suitable methods known in the art.

The nonwoven may be manufactured via a process comprising the steps of: (a) providing a precursor nonwoven; and (b) subjecting the precursor nonwoven to a deformation forming unit to form a protruded area(s) to obtain a three dimensional nonwoven, the three dimensional nonwoven comprising at least one protrusion and at least one recess wherein the protrusion comprises a first area having a first light reflectance and a second area having a second light reflectance which differs from the first light reflectance, and the recess comprises a third area having a third light reflectance.

The precursor nonwoven may be carded webs such as parallel webs, semi-random webs, random webs, cross-webs, criss-cross webs, and the like, air-laid webs, wet-laid webs, and spunbond webs, and the like.

Figure 6:
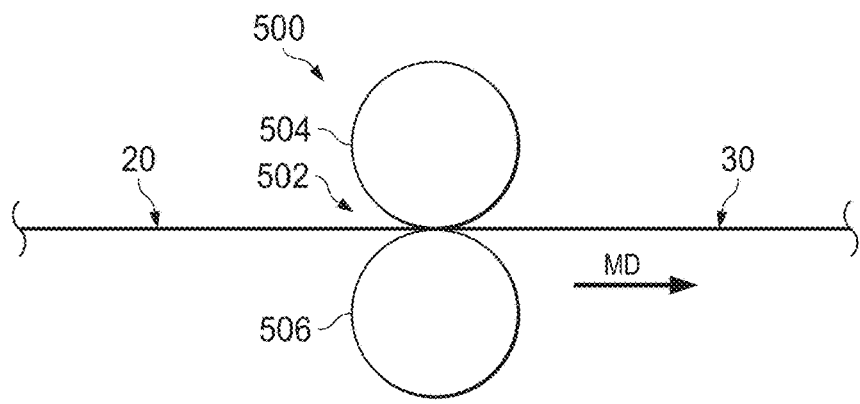
FIG. 6 is a schematic illustration of one exemplary process for forming the three dimensional nonwovens of the present disclosure.
Figure 7:
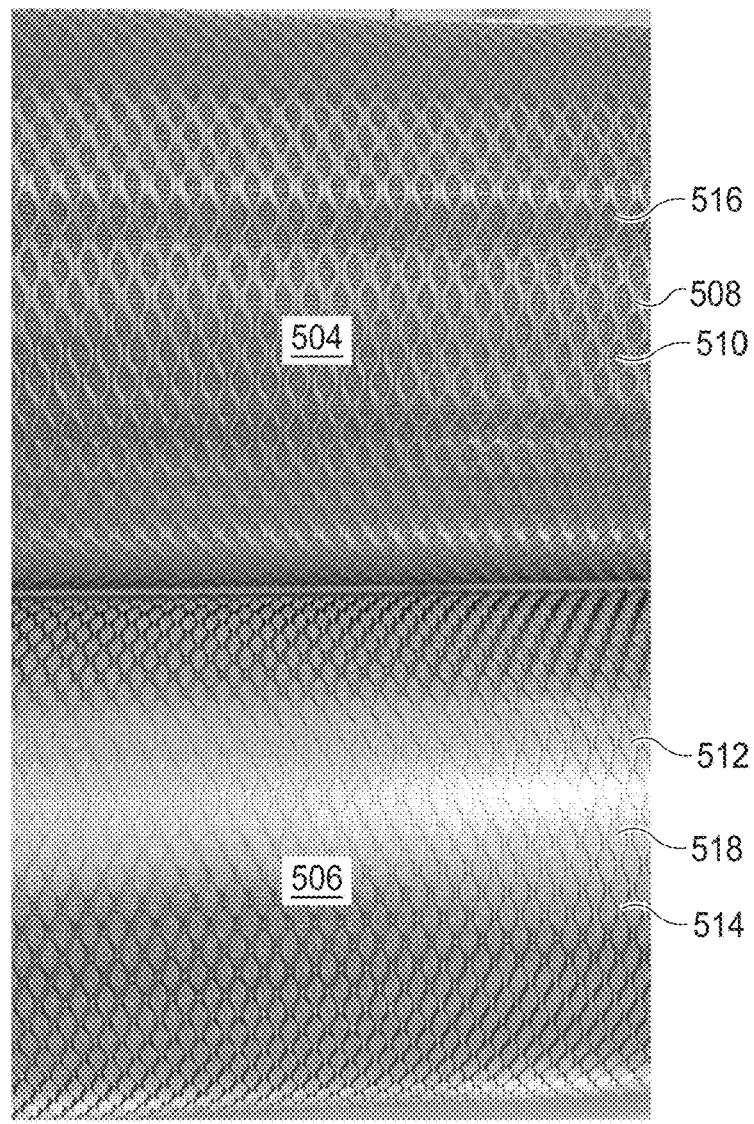
FIG. 7 is a view of intermeshing engagement of portions of a pair of rolls in accordance with the present disclosure.

Deformation of precursor nonwoven to form a three dimensional nonwoven can be conducted according to any conventionally known nonwoven deformation method. An exemplary deformation equipment is a pair of rolls comprising a first roll and a second roll. Referring to FIG. 6, precursor nonwoven 20 may be deformed by passing it through a nip 502 formed by a pair of rolls 500 having two intermeshing rolls 504 and 506, to form a three dimensional nonwoven 30. At least one of the rolls 504 and 506 may be heated. FIG. 7 shows a view of intermeshing engagement of portions of an exemplary first and a second rolls in the pair of rolls.

In one embodiment, referring to and FIGS. 1 and 2 and FIGS. 6 and 7, a first roll 504 may create the protruded area 2 and the recess having a plurality of apertures 6 in the nonwoven 30 (in combination with the second roll).

A first roll 504 may create a protruded area 2 in the three dimensional nonwoven 30 (in combination with the second roll 506) and a second roll 506 may create the recess 8 and apertures 6 in the three dimensional nonwoven 30 (in combination with the first roll 504). The first roll 504 may comprise at least one protrusion 508 extending radially outwardly from the first roll 504. The first roll 504 may also comprise a plurality of concaves 510 formed in a radial outer surface of the first roll 504. Each concave 510 may comprises a plurality of holes 516.

The second roll 506 may comprise at least one convex 512 extending radially outwardly from the second roll 506. Each convex 512 comprises a plurality of projections 518 which create apertures 6 in the three dimensional nonwoven 30 (in combination with the first roll 504). The second roll 506 may also comprise at least one groove 514 formed in the radial outer surface of the second roll 506. The grooves 514 in the second roll 506 may be configured to at least partially receive the protrusion(s) 508, thereby creating the protruded area 2 in the nonwoven 30. The groove 514 in the second roll 506 may be deep enough so that a peak of the protruded area 2 will not be compressed. Specifically, as the protrusion 508 engages into the groove 514, there is sufficient depth left in the space between the surfaces in a radial direction so that the thickness of the substrate in peak of the protruded area 2 is greater than the thickness of the recess 8. This feature provides protruded area 2 with a softer feel and a greater height compared to compressing the portions of the substrate forming the peak of the protruded area.

Figure 8A:
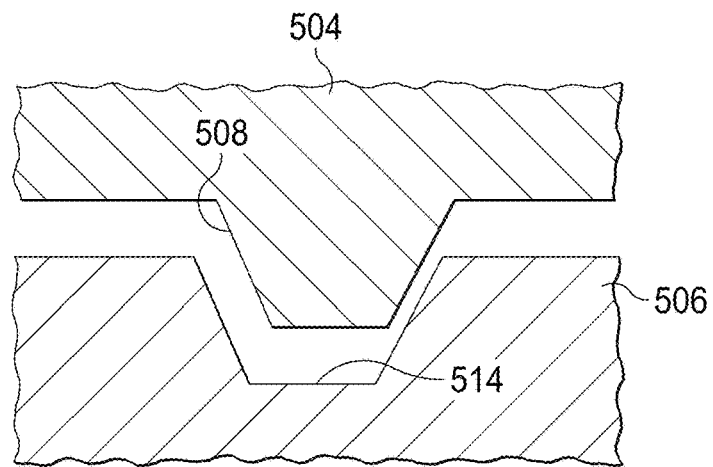
FIG. 8A is a schematic illustration of one example of intermeshing engagement of portions of a pair of rolls in accordance with the present disclosure.
Figure 8B:
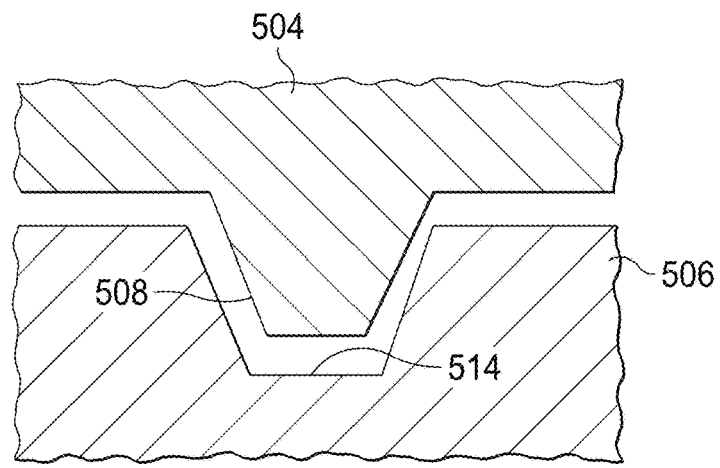
FIG. 8B is a schematic illustration of another example of intermeshing engagement of portions of a pair of rolls in accordance with the present disclosure.

FIG. 8A and FIG. 8B are schematic illustrations of exemplary intermeshing engagement of a protrusion 508 in a first roll 504 and a groove 514 in the second roll to form a protruded area 2 comprising a first area 21 and a second area 22 in accordance with the present disclosure.

In one embodiment, to create the second area 22 in the wall of the protruded area 2, referring to FIG. 8A, the groove 514 in the second roll 506 may be configured to at least partially receive the protrusion 508 in the first roll in such a way that a gap between a first sidewall of the protrusion 508 and a first sidewall of the groove 514 facing the first sidewall of the protrusion 508 is bigger than a gap between a second sidewall of the protrusion 508 and second sidewall of groove 514 facing the second sidewall of the protrusion 508.

In another embodiment, to create the second area 22 in the wall of the protruded area 2, at least a first sidewall of the protrusion 508 and a first sidewall of the groove 514 facing the first sidewall of the protrusion 508 have different slope angle, so that the first sidewall of the protrusion 508 and the first sidewall of the groove 514 are not parallel to each other and at least the side gap between the first sidewall of the protrusion 508 and the first sidewall of the groove 514 has inconsistent gap. One example of such a configuration is illustrated in FIG. 8B.

The concave 510 in the first roll 505 may be configured with the convex 512 in the second roll 506 in such a way that the concave 510 and the holes 516 in the first roll 504 at least partially receive the convex 512 and the projections 518 in the second roll 506 thereby creating the recesses 8 and the apertures 6 in the three dimensional nonwoven 30.

Absorbent Article

An absorbent article of the present disclosure comprises a skin-facing surface, a garment-facing surface, a liquid pervious topsheet, a liquid impervious backsheet, an absorbent core disposed between the topsheet and the backsheet, and a three dimensional nonwoven disclosed herein. In one embodiment, the liquid permeable topsheet comprises the three-dimensional nonwoven. In another embodiment, the three dimensional nonwoven of the present disclosure forms at least part of the garment-facing surface.

Figure 9:
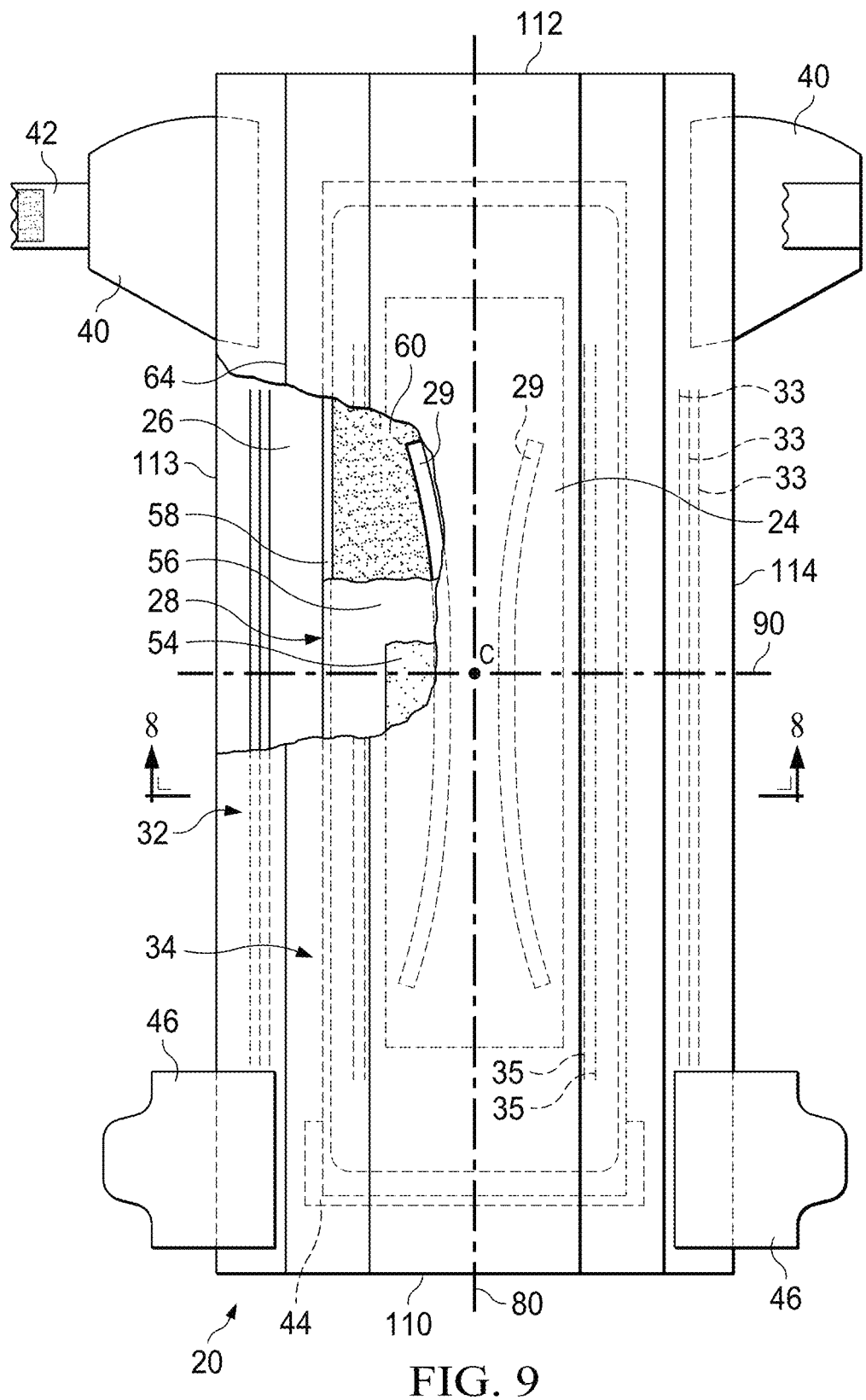
FIG. 9 is a schematic plan view of an exemplary absorbent article according to the present disclosure.

Absorbent articles will now be generally discussed and further illustrated in the form of a baby diaper 1 as exemplarily represented in FIG. 9. FIG. 9 is a plan view of the exemplary diaper 1 in a flattened-out configuration with the taped ends opened and the garment-facing side turned up. An article that is presented to the user closed such as a training pant may also be represented flattened out by cutting it along its side waists. The absorbent article will typically have a front edge 110, a back edge 112 and the longitudinally-extending lateral side edges 113, 114. The front edge 110 forms the edge of the front waist and the back edge 112 of the back waist, which together when worn by the wearer form the opening for the waist of the wearer. The lateral edges 113, 114 can each form one of the leg openings. The absorbent article 100 notionally comprises a longitudinally centerline 80 dividing the article in a left side and a right side, and a perpendicular transversal centerline 90 disposed at half the length of the article as measured on the longitudinal centerline 80, with both centerlines crossing at the center point C. The taped back ends 42 attached on the front of the diaper to such as a landing zone 44.

Figure 10:
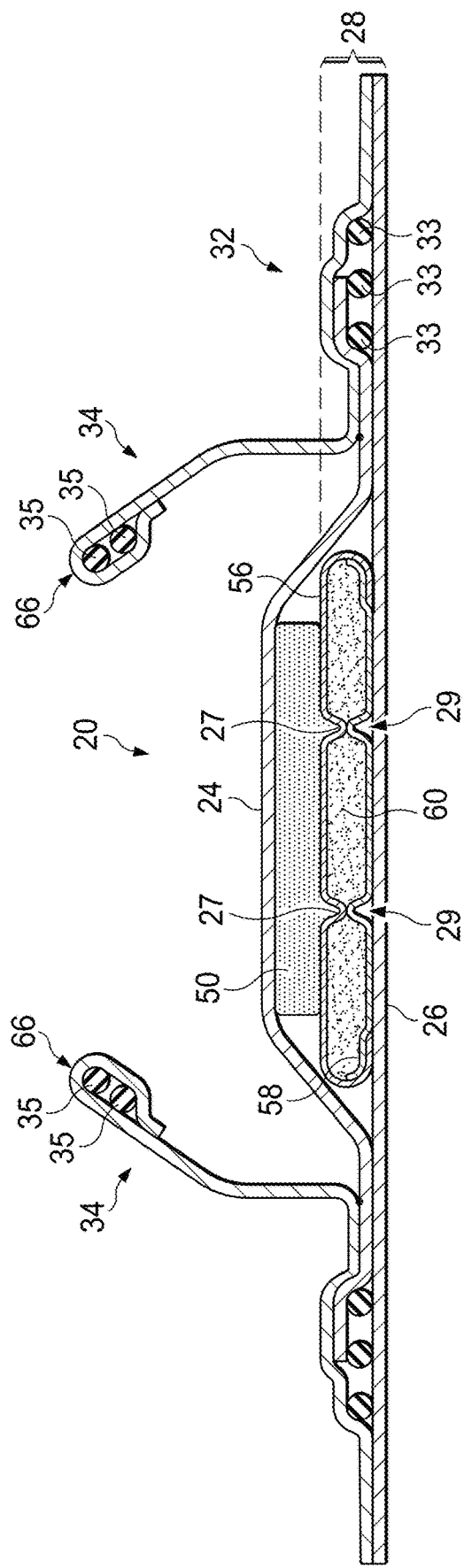
FIG. 10 is a lateral cross-section along 2-2 of the absorbent article of FIG. 9.

Other layers of the absorbent article are better illustrated in FIG. 10, which shows in cross-section in addition to the liquid permeable topsheet 24 and the backsheet 26, an absorbent core 28 between the topsheet 24 and the backsheet 26.

A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers.

Figure 11:
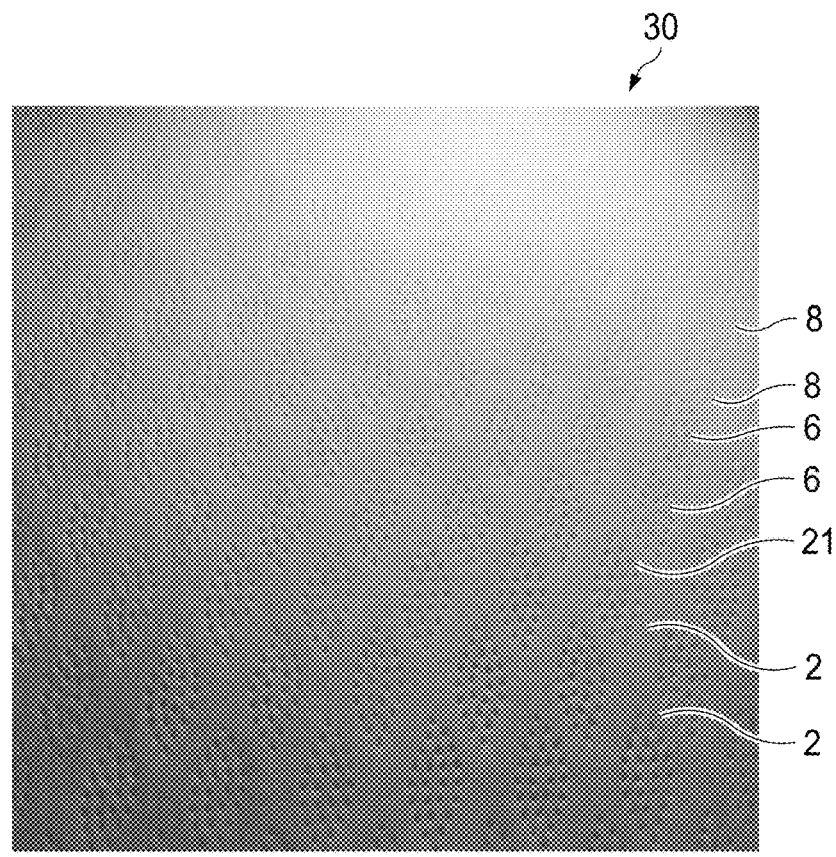
FIG. 11 is a plan view of Nonwoven 3.

An optional acquisition and/or distribution layer (or system) 54 is represented in FIG. 11 together with other typical diaper components. The acquisition and/or distribution layer may comprise one layer or more than one layer. Typical acquisition and/or distribution layers may not comprise SAP as this may slow the acquisition and distribution of the fluid, but an additional layer may also comprise SAP if some fluid retention properties are wished.

The absorbent article may typically comprise a pair of partially upstanding barrier leg cuffs 34 having elastic elements 35 and elasticized gasketing cuffs 32 having elastic elements 33 substantially planar with the chassis. Both types of cuffs are typically joined to the chassis of the absorbent article typically via bonding to the topsheet and/or backsheet.

The absorbent article may comprise elasticized back ears 40 having a tape end 42 which can be attached to a landing zone 44 at the front of the article, and front ears 46 typically present in such taped diapers to improve containment and attachment.

Absorbent Core

As used herein, the term "absorbent core" refers to a component used or intended to be used in an absorbent article and which comprises an absorbent material and optionally a core wrap. As used herein, the term "absorbent core" does not include the topsheet, the backsheet and any acquisition-distribution layer or multilayer system, which is not integral part of the absorbent core. The absorbent core is typically the component of an absorbent article that has the most absorbent capacity of all the components of the absorbent article. The terms "absorbent core" and "core" are herein used interchangeably.

Referring to FIGS. 9 and 10, the absorbent core 28 can absorb and contain liquid received by the absorbent article and comprise an absorbent material 60, which may be cellulose fibers, a blend of superabsorbent polymers and cellulose fibers, pure superabsorbent polymers, and/or a high internal phase emulsion foam. The absorbent core 28 may comprise absorbent material free channels 29, through which the top side 56 of the core wrap may be bonded to the bottom side 58 of the core wrap. The core wrap bonds 27 may at least persist as the absorbent core 28 swells upon liquid absorption and creates three dimensional channels at the wearer-facing surface of the article. Of course, this is entirely optional, the absorbent core may also not have bonded channels, or even unbonded channels. The absorbent material defines an absorbent material area 8, which may be rectangular as show in in FIG. 9, but it is also common to have a shaped area which is tapered in the area around the transversal centerline 90.

The absorbent material comprises a liquid-absorbent material commonly used in disposable absorbent articles such as comminuted wood pulp, which is generally referred to as airfelt or fluff. Examples of other suitable liquid-absorbent materials include creped cellulose wadding; melt blown polymers, including co-form; chemically stiffened, modified or cross-linked cellulosic fibers; tissue, including tissue wraps and tissue laminates, absorbent foams, absorbent sponges, superabsorbent polymers (herein abbreviated as "SAP"), absorbent gelling materials, or any other known absorbent material or combinations of materials.

The absorbent material in the absorbent core can be any type. It can be an airfelt core comprising wood cellulose fibers such as pulp fibers mixed with SAP, or an airfelt-free core free from such cellulose fibers. Airfelt cores typically comprises from 40% to 80% of SAP. For absorbent cores comprising a relatively high proportion of SAP at least partially enclosed within the core wrap, the SAP content may represent in particular at least 80%, 85%, 90%, 95% and up to 100%, of superabsorbent polymer by weight of the absorbent material. The absorbent material may in particular comprise no or only small amount of cellulose fibers, such as less than 20%, in particular less than 10%, 5% or even 0% of cellulose fibers by weight of the absorbent material. The absorbent core may comprise an absorbent material comprising at least 80%, at least 90%, at least 95%, or at least 99% by weight of the absorbent core. The term "superabsorbent polymer" refers herein to absorbent material, which may be cross-linked polymer, and that can typically absorb at least 10 times their weight of an aqueous 0.9% saline solution as measured using the Centrifuge Retention Capacity (CRC) test (EDANA method WSP 241.2-05E). The SAP may in particular have a CRC value of more than 20 g/g, or more than 24 g/g, or of from 20 to 50 g/g, or from 20 to 40 g/g, or from 24 to 30 g/g. The SAP may be typically in particulate forms (superabsorbent polymer particles), but it not excluded that other forms of SAP may be used such as a superabsorbent polymer foam for example.

Backsheet

An absorbent article according to the present disclosure comprises a liquid impervious backsheet. The backsheet may be designed to prevent the exudates absorbed by and contained within the absorbent article from soiling articles that may contact the absorbent article, such as bed sheets and undergarments. The backsheet may be substantially water-impermeable. Suitable backsheet materials may include breathable materials that permit vapors to escape from the absorbent article while still preventing exudates from passing through the backsheet. The backsheet may comprise a liquid impermeable film. The backsheet may comprise a wetness indicator.

Outer Cover

An absorbent article according to the present disclosure may comprise an outer cover forming at least part of a garment-facing surface of the absorbent article. The outer cover may comprise a three dimensional nonwoven disclosed herein in such a way that a first side having protrusions of the substrate forms at least part of the garment-facing side of the article. When a backsheet comprises a liquid impermeable polymer film, the polymer film and the substrate disclosed herein may be disposed in a face to face relationship in such a way that the substrate is towards the garment-facing side of the article, and the film is towards an absorbent core of the article. The first layer is oriented outwardly relative to the article, so that the protrusions can be felt by the caretaker or a user feeling the garment-facing side of the article.

The absorbent article may also comprise other typical components, which are not represented, such as a back-elastic waist feature, a front elastic waist feature, transverse barrier cuff(s), a lotion application, etc.

Components of the disposable absorbent article described in this specification can at least partially be comprised of bio-sourced content as described in US 2007/0219521A1 Hird et al published on Sep. 20, 2007, US 2011/0139658A1 Hird et al published on Jun. 16, 2011, US 2011/0139657A1 Hird et al published on Jun. 16, 2011, US 2011/0152812A1 Hird et al published on Jun. 23, 2011, US 2011/0139662A1 Hird et al published on Jun. 16, 2011, and US 2011/0139659A1 Hird et al published on Jun. 16, 2011. These components include, but are not limited to, topsheet nonwovens, backsheet films, backsheet nonwovens, side panel nonwovens, barrier leg cuff nonwovens, super absorbent, nonwoven acquisition layers, core wrap nonwovens, adhesives, fastener hooks, and fastener landing zone nonwovens and film bases. In at least one embodiment, a disposable absorbent article component comprises a bio-based content value from about 10% to about 100% using ASTM D6866-10, method B, in another embodiment, from about 25% to about 75%, and in yet another embodiment, from about 50% to about 60% using ASTM D6866-10, method B. In order to apply the methodology of ASTM D6866-10 to determine the bio-based content of any disposable absorbent article component, a representative sample of the disposable absorbent article component must be obtained for testing. In at least one embodiment, the disposable absorbent article component can be ground into particulates less than about 20 mesh using known grinding methods (e.g., Wiley® mill), and a representative sample of suitable mass taken from the randomly mixed particles.

Test Methods

1. Light Reflectance Test

The Light Reflectance Test measures the amount of light reflected from a visually discernable area on the surface of the three-dimensional nonwoven illuminated by direct light at an incident angle of approximately 67 degrees. It is based on analysis of a calibrated grayscale digital image of the illuminated sample surface using an image analysis program (a suitable program is ImageJ v. 1.52, National Institute of Health, USA, or equivalent).

(1) Sample Preparation

To obtain a sample for measurement, lay a dry substrate raw material out flat and cut to an appropriate size for analysis.

If the substrate material is a layer of an absorbent article, for example a topsheet, backsheet nonwoven, acquisition layer, distribution layer, or another component layer; tape the absorbent article to a rigid flat surface in a planar configuration. Carefully separate the individual substrate layer from the absorbent article. A scalpel and/or cryogenic spray (such as Cyto-Freeze, Control Company, Houston TX) can be used to remove a substrate layer from additional underlying layers, if necessary, to avoid any longitudinal and lateral extension of the material.

If the substrate material is in the form of a wet wipe, open a new package of wet wipes and remove the entire stack from the package. Remove a single wipe from the middle of the stack, lay it out flat and allow it to dry completely prior to analysis.

A sample may be obtained from any location containing the visually discernible areas to be analyzed. An area may be visually discernable due to changes in texture, height, specular light reflectance, or thickness. Care should be taken to avoid folds, wrinkles or tears when selecting a location for sampling and analysis.

(2) Image Acquisition

Sample and calibration images were taken using a lab-built image acquisition system. The key components include a DSLR camera (Canon EOS 6D Mark 2) with a lens (EF 24-105 mm f/4L IS 2 USM lens, or equivalent), a non-reflective black background plate, and a bar light (Smart Vision Lights LHF 300, Muskegon, MI, or equivalent). The bar light is placed 700 mm away from the sample in the horizontal direction and 300 mm away from the sample in the vertical direction, such that the directed light has an angle of incidence of approximately 67 degrees. The sample is laid horizontally flat at the center of the black background plate, directly beneath and centered within the field of view of the camera mounted 800 mm directly above, rotated to maximize the amount of specular reflectance from the identified areas (e.g. melt lines), and an image is acquired. Next, acquire an image of a calibrated color standard target containing 24 standard color chips (ColorChecker Passport, available from X-Rite; Grand Rapids, MI, or equivalent) positioned at the same location as the sample and under the same imaging conditions. Lastly, acquire an image of a plain white background under the same lighting and imaging conditions. The camera's manual settings are set so that the image is properly exposed, such that there is no signal clipping in any of the color channels. Suitable settings might be a focal length of the camera set to 105 mm, ISO: 100, F stop: 8.0, Shutter speed: 1/15 sec. Using a standard 18% gray card (e.g., Munsell 18% Reflectance (Gray) Neutral Patch/Kodak Gray Card R-27, available from X-Rite; Grand Rapids, MI, or equivalent), the camera's white balance is custom set for the lighting conditions. Each image is properly focused, captured, and saved as a 24-bit RGB JPEG file. The resulting images must be at a resolution of at least 18 pixels/mm (3) Image Calibration The sample, color standard, and background image files are opened in the image analysis software. First, convert all three RGB images to CIELAB color space and extract only the L* channel image from each for further analysis. Next, use the background image to flatten the lighting gradient present in the sample and color standard images. Create a calibration curve using the measured average L* values from each of the six monochromatic grayscale chips in the image of the color standard and their reported true L* values provided with the color standard target. Lastly, apply the calibration curve transform to correct the L* pixel values in the sample image and distance calibrate the image.

(4) Light Reflectance Measurement

To measure the light reflectance of an area (e.g. the first area, the second area, the third area) begin by identifying the boundaries of three distinct adjacent areas. The boundary of an area is identified by visual discernment of differences in physical properties when compared to other areas within the sample. For example, an area boundary can be identified based by visually discerning a thickness or height difference when compared to another area in the sample. Differences in physical properties such as height, thickness, texture, or specular reflection of light can be used to discern area boundaries on either the physical sample itself, cross-sectional images, topography images, or light reflection images.

Figure 17:
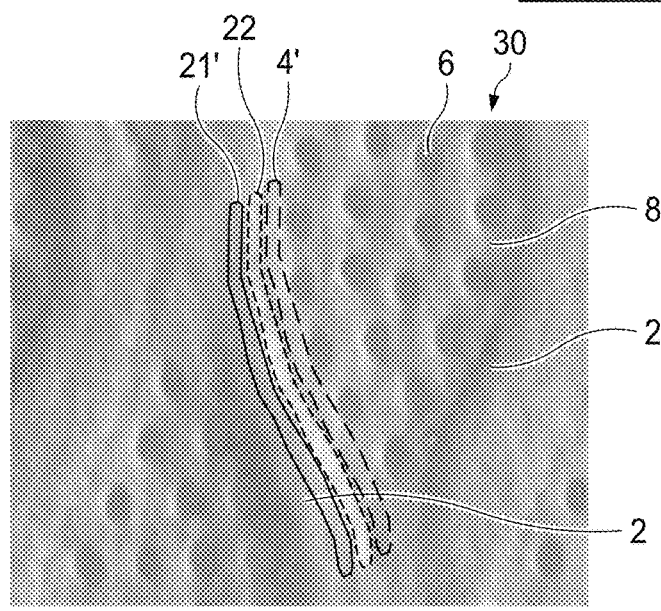
FIG. 17 is an image illustrating measurement of a light reflectance in a nonwoven.

Referring to FIG. 17, using the image analysis software, manually draw a line tracing an enclosed "region of interest" (ROI) along the identified boundary of the area having the greatest specular reflectance i.e., the second area 22. Once the boundary of that region has been drawn, make two copies of the ROI and place one on either side of the initial ROI, within the identified boundaries of the two adjacent areas, i.e, an area 21' in the first area 21, and area 4' in the third area 4. The average L* values are measured from within each of the three ROIs and recorded as a light reflectance for each of the three individual areas to the nearest tenth. Additionally, measure and record the boundary ROI's area to the nearest 0.1 mm$^2$ and the maximum feret diameter to the nearest 0.1 mm The maximum ferret diameter is considered a ROI length. This procedure is repeated at two other identified replicate locations representing the first area 21 and the third area 4 and their individual light reflectances are measured and recorded accordingly. The arithmetic mean of the three recorded values from each of the three distinct areas is calculated and reported as their Reflectance Value to the nearest tenth. Additionally, calculate and report the average boundary ROI area and maximum feret diameter (ROI length).

2. Thickness Test

The Thickness Test measures the cross-sectional thickness of an identified sample area using an optical microscope equipped with a digital camera to capture an image. Linear distances within the captured image are measured using image analysis software appropriate for making calibrated distance measurements (a suitable software is ImageJ v. 1.52, National Institute of Health, USA, or equivalent).

(1) Sample Preparation

A sample for measurement is prepared according to (1) Sample Preparation under Light Reflectance Test, supra.

(2) Image Acquisition

Samples are mounted to a rigid plate such that the cross-sectioned edge is left unconstrained and unobstructed when viewed through the microscope. The mounted sample is placed beneath the objective and oriented such that the cross-sectioned edge is viewed face on. Reflected illumination from a directed light source is used to illuminate the sample. The image is focused at the cross-sectioned edge surface and a properly exposed digital image is captured. Additionally, an image of a calibrated ruler is captured in the same position and manner as the sample. The acquired digital images must have a resolution of at least 1 micron per pixel.

(3) Thickness Measurement

The acquired images are imported into the image analysis software and the sample image spatially calibrated against the certified ruler image. Spatial calibration is used to establish pixel size and allow for conversion to standard units. Using the image analysis software, the distance between the upper and lower sample surfaces at the cross-sectional edge surface and within each of the adjacent identified areas is measured and recorded. A total of five replicate thickness measurements are made on each of the identified areas from three replicate samples. The arithmetic mean of the five recorded measurements from each of the adjacent areas is calculated and each is reported as its thickness to the nearest micron.

EXAMPLES

Example 1. Nonwoven Preparation 35 gsm carded air-through nonwoven was prepared from 2 denier PET/PE core/sheath bicomponent fibers and used as precursor nonwoven.

Nonwoven 1

The obtained 35 gsm carded air-through nonwoven was put into a mechanical embossing-aperturing process illustrated in FIG. 6 using a pair of rolls shown in FIG. 7 to produce Nonwoven 1 having features shown in FIGS. 1-3.

A protrusion 508 in a first roll 504 and a groove 514 in the second roll 506 to be engaged with each other had a configuration illustrated in FIG. 8A. That is, a first sidewall of the protrusion 508 was parallel to a first sidewall of the groove 514 facing the first sidewall of the protrusion 508, and a second sidewall of the protrusion 508 was parallel to a second sidewall of the groove 514 facing the second sidewall of the protrusion 508, and the side gap between the first sidewall of the protrusion 508 and the first sidewall of the groove 514 was narrower than the side gap between the second sidewall of the protrusion 508 and the second sidewall of the groove 514. The embossing-aperturing process formed a first area 21 and a second area 22 in the protruded area 2.

Nonwoven running speed was about 25 meter/min. Temperatures of a first roll and a second roll were 83° C. and 73° C., respectively.

Nonwoven 2

Figure 4:
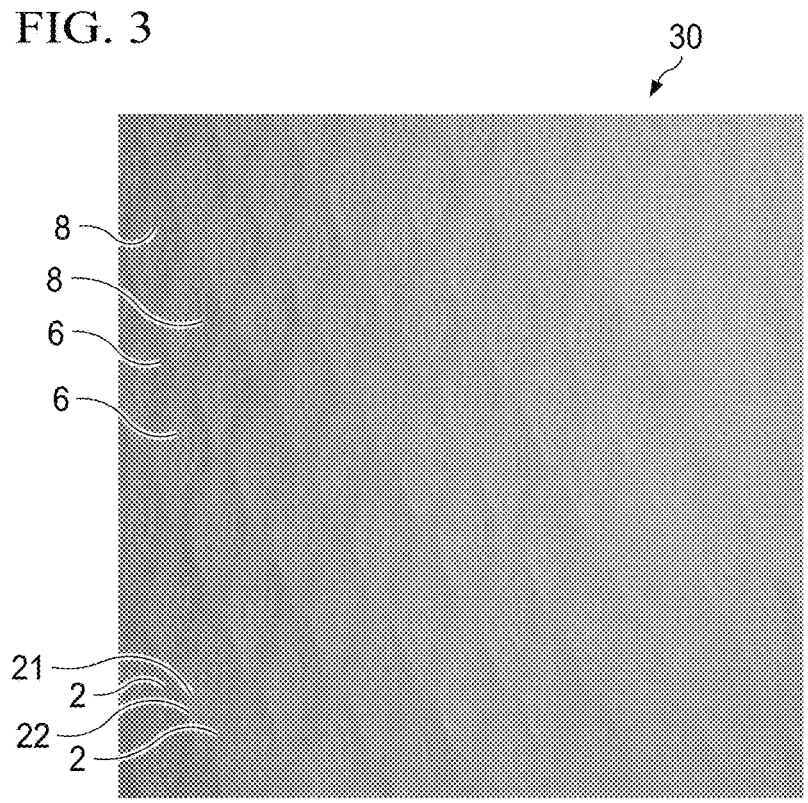
FIG. 4 is a plan view of another nonwoven according to the present disclosure.
Figure 5:
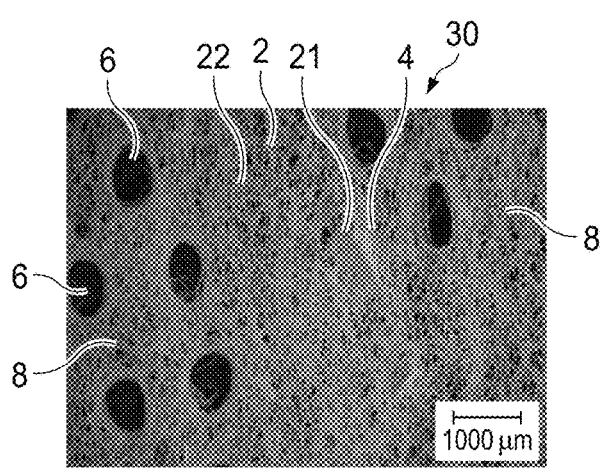
FIG. 5 is a magnified plan view of part of the nonwoven of FIG. 4.

Three dimensional nonwoven (Nonwoven 2) having features shown in FIGS. 4 and 5 was produced using the 35 gsm carded air-through nonwoven according to the process disclosed with respect to Nonwoven 1 above except for temperatures of a first roll and a second roll being 77° C. and 67° C., respectively.

Nonwoven 3

Figure 12:
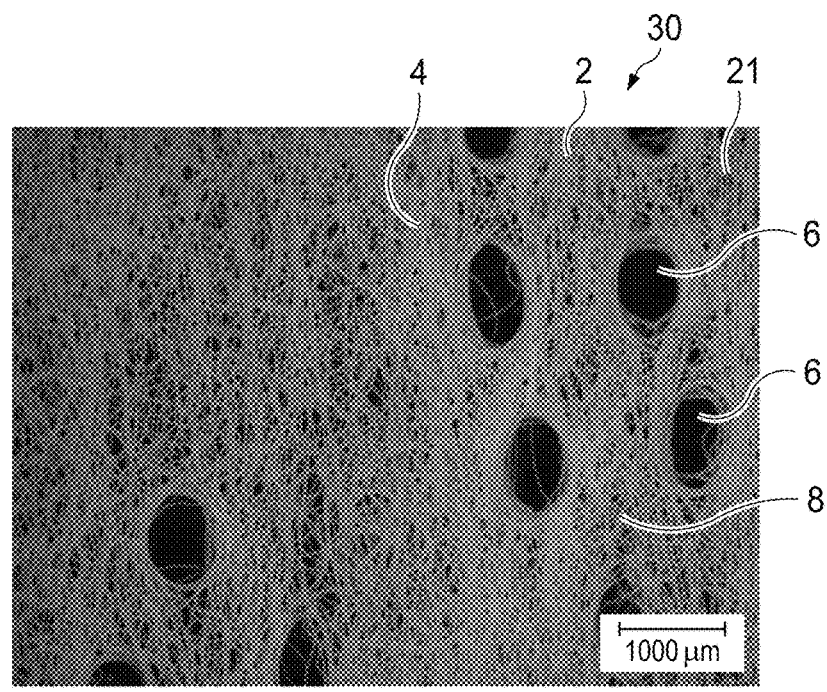
FIG. 12 is a magnified plan view of part of the nonwoven of FIG. 11.
Figure 13:
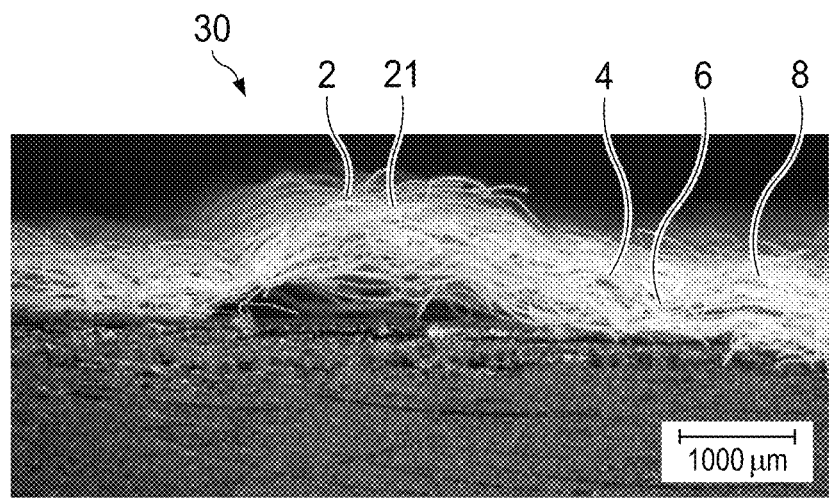
FIG. 13 is a partial cross-section view of the nonwoven of FIG. 11.

Nonwoven 3 having features shown in FIGS. 11-13 was produced using the 35 gsm carded air-through nonwoven. FIG. 11 is a plan view of Nonwoven 3, and FIG. 12 is a magnified plan view of part of Nonwoven 4. FIG. 13 is a partial cross-section view of nonwoven 3.

Figure 8C:
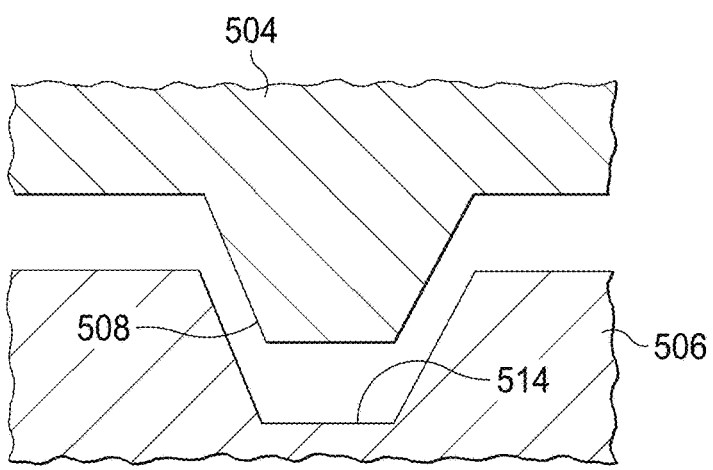
FIG. 8C is a schematic illustration of conventional intermeshing engagement of portions of a pair of rolls.

The 35 gsm carded air-through nonwoven was put into a mechanical embossing-aperturing process illustrated in FIG. 6 comprising a pair of rolls having a configuration similar to one in FIG. 7 to produce Nonwoven 3. In the pair of rolls, a protrusion 508 in a first roll 504 and a groove 514 in the second roll 506 to be engaged with each other had a configuration illustrated in FIG. 8C. That is, a first sidewall of the protrusion 508 was parallel to a first sidewall of the groove 514 facing the first sidewall of the protrusion 508, and a second sidewall of the protrusion 508 was parallel to a second sidewall of the groove 514 facing the second sidewall of the protrusion 508, and the side gap between the first sidewall of the protrusion 508 and the first sidewall of the groove 514 and the side gap between the second sidewall of the protrusion 508 and the second sidewall of the groove 514 are substantially identical. As a result, protruded area 2 in Nonwoven 3 was formed upon homogenous heat-compression, and it did not have a second area having a light reflectance different from a first area of the protruded area, referring to FIGS. 11-13.

Nonwoven 4

Figure 14:
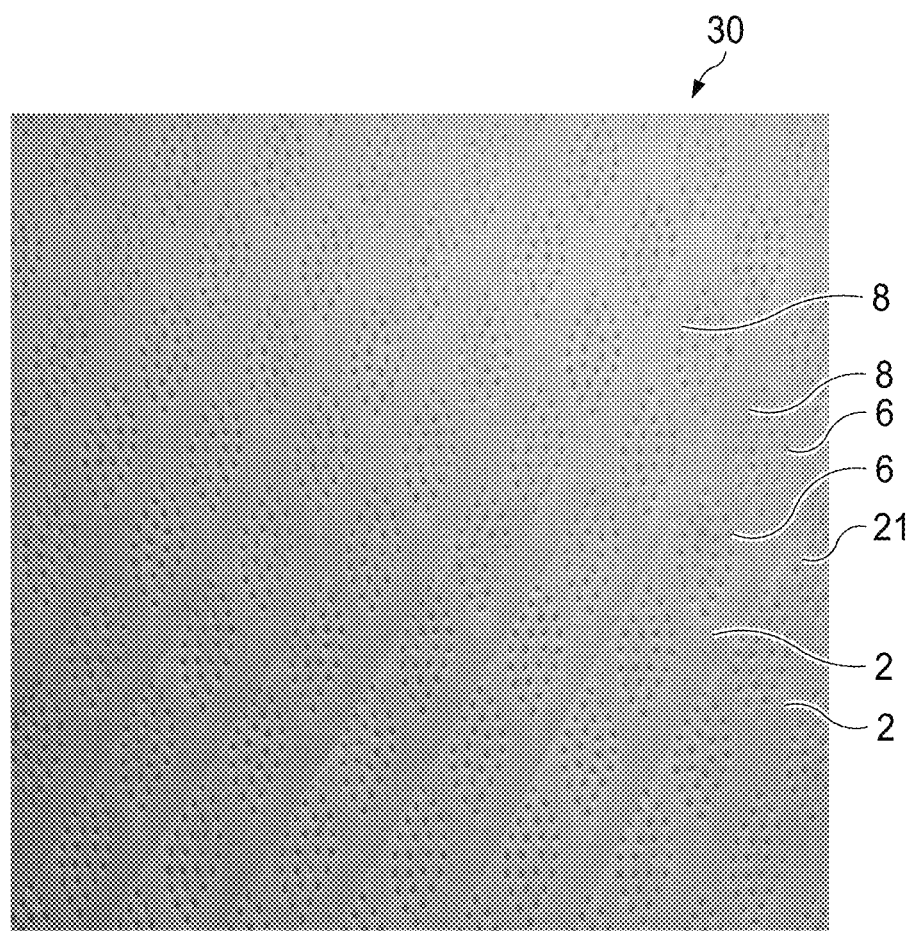
FIG. 14 is a plan view of Nonwoven 4.
Figure 15:
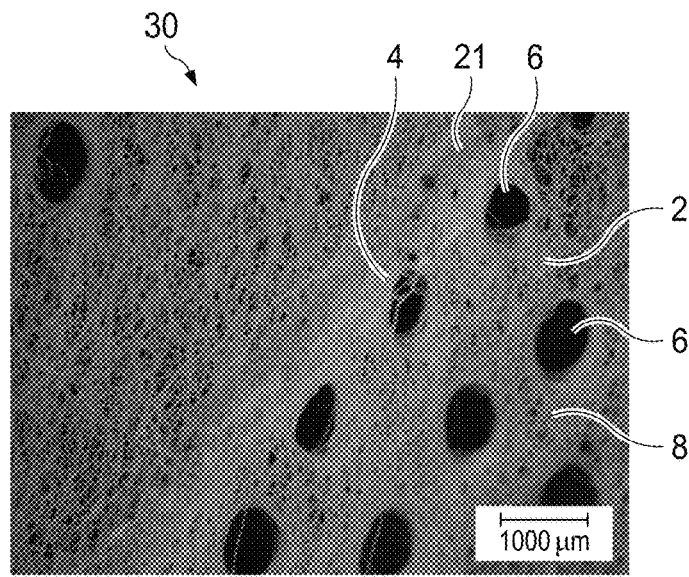
FIG. 15 is a magnified plan view of part of the nonwoven of FIG. 14.
Figure 16:
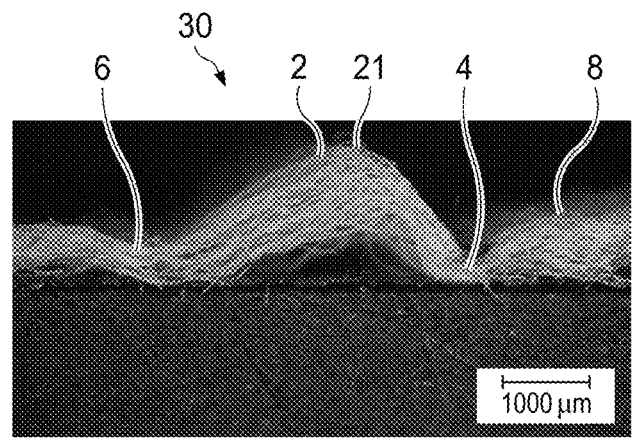
FIG. 16 is a partial cross-section view of the nonwoven of FIG. 14.

Nonwoven 4 having features shown in FIGS. 14-16 was produced using the 35 gsm carded air-through nonwoven. The 35 gsm carded air-through nonwoven was put into a mechanical embossing-aperturing process the same as one to produce Nonwoven 3 above. A heat-fused area 4 in a recess 8 was formed using a heated meshed metal on Nonwoven 4. FIG. 14 is a plan view of Nonwoven 4, and FIG. 15 is a magnified plan view of part of Nonwoven 4. FIG. 16 is a partial cross-section view of nonwoven 4. Referring to FIGS. 14-16, Nonwoven 4 has the same nonwoven configuration as Nonwoven 3 except that recess 8 has a heat-fused area, a third area 4.

Example 2. Physical Properties of Nonwovens

Light reflectances, and areas and the maximum feret diameter of the second areas in Nonwovens 1 and 2 were measured according to Light Reflectance Test. Thicknesses of Nonwovens 1 and 2 were measured according to Thickness Test disclosed herein. All results are indicated in Table 1 below.

TABLE 1

|  |  | Nonwoven 1 | Nonwoven 2 |
|---|---|---|---|
| Thickness (μm) | First area | 709.1 | 648.4 |
|  | Second area | 50.4 | 57.7 |
|  | Third area | 340.5 | 314.9 |
| Area of the second area (mm²) |  | 3.8 | 2.2 |
| Maximum feret diameter of the second area* (mm) |  | 10.2 | 5.3 |
| Light reflectance | First area | 98.8 | 99.9 |
|  | Second area | 112.2 | 108.8 |
|  | Third area | 98.5 | 96.8 |

Maximum feret diameter of the second area*: Length of the second area*

Example 3. Evaluation of Nonwoven Softness

Nonwovens 1-3 prepared in Example 1 were tested for nonwoven softness with 5 trained panels using a degree of difference ("DoD") test between two test samples. The difference is scaled by 5 scores, i.e. 1-5 as below.
Score 1: No difference
Score 2: Slight difference, which can be told by well-trained softness panel, but cannot be told by consumers
Score 3: Noticeable difference
Score 4: Significant difference
Score 5: Outside normal range

TABLE 2

| Softness DoD score | | |
|---|---|---|
| Test Leg | Test nonwoven | Score |
| Leg 1 | Nonwoven 1 over Nonwoven 3 | 1 |
| Leg 2 | Nonwoven 2 over Nonwoven 3 | 2 |

Example 4. Evaluation of Three Dimensional Visibility

Nonwovens 2,3 and 4 prepared in Example 1 were tested for three dimensional impression of patterns in each nonwoven with 15 panels. First, 3 nonwoven samples of Nonwoven 2 and Nonwoven 3 were shown to each panel in a given sequence indicated in Table 3 below. When a panel correctly picked up the correct different sample among three samples, and commented pattern visibility, the result was recorded as positive. All results are indicated in Table 3 below.

Otherwise, the result was recorded as negative. Then, the same test was conducted using samples of Nonwoven 2 and Nonwoven 4 where 3 nonwoven samples of Nonwoven 2 and Nonwoven 4 were shown to each panel in a given sequence indicated in Table 4 below. All results are indicated in Table 4 below.

TABLE 3

| Panel No. | Sample sequence | | | Picked-up as a different one | Comments | Result |
|---|---|---|---|---|---|---|
| 1 | A* | A | B* | B | B looks much flatter than A | Positive |
| 2 | A | B | A | B | B looks much flatter than A | Positive |
| 3 | A | B | B | A | A is a 3D material, but B looks like a 2D flat material | Positive |
| 4 | B | A | A | B | B looks much flatter than A | Positive |
| 5 | B | A | B | A | A looks more 3D than B | Positive |
| 6 | B | B | A | A | B looks much flatter than A | Positive |
| 7 | A | A | B | B | A looks more 3D than B | Positive |
| 8 | A | B | A | B | B looks much flatter than A | Positive |
| 9 | A | B | B | A | B looks much flatter than A | Positive |
| 10 | B | A | A | B | B looks much flatter than A | Positive |
| 11 | B | A | B | A | B looks much flatter than A | Positive |
| 12 | B | B | A | A | B looks much flatter than A | Positive |
| 13 | A | A | B | B | A looks more 3-D than B | Positive |
| 14 | A | B | A | B | B looks much flatter than A | Positive |
| 15 | A | B | B | A | B looks much flatter than A | Positive |

A*: Nonwoven 2
B*: Nonwoven 3

TABLE 4

| Panel No. | Sample consequence | | | Picked-up as a different one | Comments | Result |
|---|---|---|---|---|---|---|
| 1 | A* | A | C* | C | C looks like a flat material with lines, but not 3D material | Positive |
| 2 | A | C | A | C | C looks like a flat material with lines, but not 3D material | Positive |
| 3 | A | C | C | N/A | Cannot tell the difference | Negative |
| 4 | C | A | A | C | C looks like a flat material with lines, but not 3D material | Positive |
| 5 | C | A | C | A | A looks more 3D than C | Positive |
| 6 | C | C | A | A | C looks like a flat material with lines, but not 3D material | Positive |
| 7 | A | A | C | C | C looks like a flat material with lines, but not 3D material | Positive |
| 8 | A | C | A | C | C looks like a flat material with lines, but not 3D material | Positive |
| 9 | A | C | C | A | A looks more 3D than C | Positive |
| 10 | C | A | A | C | C looks like a flat material with lines, but not 3D material | Positive |
| 11 | C | A | C | A | C looks like a flat | Positive |

TABLE 4-continued

| Panel No. | Sample consequence | | | Picked-up as a different one | Comments | Result |
|---|---|---|---|---|---|---|
| 12 | C | C | A | N/A | material with lines, but not 3D material Cannot tell the difference | Negative |
| 13 | A | A | C | C | C looks like a flat material with lines, but not 3D material | Positive |
| 14 | A | C | A | C | C looks like a flat material with lines, but not 3D material | Positive |
| 15 | A | C | C | A | A looks more 3D than C | Positive |

A*: Nonwoven 2
C*: Nonwoven 4

In most of tested legs with 15 panel, Nonwoven 2 was evaluated to have distinctively better pattern impression than Nonwoven 3 and Nonwoven 4.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A three dimensional nonwoven comprising:
   one or more protruded areas comprising a first area having a first light reflectance and a second area having a second light reflectance, and
   one or more recesses comprising a third area having a third light reflectance,
   wherein the first light reflectance is different from the second light reflectance, as measured according to Light Reflectance Test; and
   wherein the three dimensional nonwoven comprises:
      at least one continuous protruded area of the one or more protruded areas surrounding a plurality of discrete recesses of the one or more recesses, or
      at least one continuous recess of the one or more recesses surrounding a plurality of discrete protruded areas of the one or more protruded areas.

2. The three dimensional nonwoven of claim 1, wherein the difference between the first light reflectance and the second light reflectance is no less than 6, as measured according to Light Reflectance Test.

3. The three dimensional nonwoven of claim 1, wherein the difference between the second light reflectance and the third light reflectance is no less than 6, as measured according to Light Reflectance Test.

4. The three dimensional nonwoven of claim 1, wherein the second area has a length no less than 3 mm, as measured according to Light Reflectance Test.

5. The three dimensional nonwoven of claim 1, wherein the first area has a first thickness and the second area has a second thickness different from the first thickness, the second thickness being no greater than 100 μm, as measured according to Thickness Test.

6. The three dimensional nonwoven of claim 1, wherein the second area is located in a wall of at least one of the one or more protruded areas.

7. The three dimensional nonwoven of claim 1, wherein at least one of the one or more recesses comprises a plurality of elements selected from the group of apertures, embosses, and combinations thereof.

8. The three dimensional nonwoven of claim 1, wherein the second area is a highly heat-fused area.

9. The three dimensional nonwoven of claim 1, wherein the second area is located along at least part of a periphery of at least one of the one or more recesses.

10. The three dimensional nonwoven of claim 1, wherein the three dimensional nonwoven comprises a plurality of the one or more recesses.

11. The three dimensional nonwoven of claim 1, wherein the three dimensional nonwoven comprises a PET/PE core/sheath bicomponent fiber.

12. An absorbent article comprising a skin-facing surface, a garment-facing surface, a liquid permeable topsheet, a liquid impermeable backsheet, an absorbent structure disposed between the topsheet and the backsheet, and a three dimensional nonwoven,
   wherein the three dimensional nonwoven comprises:
      one or more protruded areas comprising a first area having a first light reflectance and a second area having a second light reflectance, and
      one or more recesses comprising a third area having a third light reflectance,
      wherein the first light reflectance is different from the second light reflectance, as measured according to Light Reflectance Test; and
      wherein the three-dimensional nonwoven comprises:
         at least one continuous protruded area of the one or more protruded areas surrounding a plurality of discrete recesses of the one or more recesses, or
         at least one continuous recess of the one or more recesses surrounding a plurality of discrete protruded areas of the one or more protruded areas.

13. The absorbent article of claim 12, wherein the difference between the first light reflectance and the second light reflectance is no less than 6, as measured according to Light Reflectance Test.

14. The absorbent article according to claim 12, wherein the second area has a length no less than 3 mm, as measured according to Light Reflectance Test.

15. The absorbent article according to claim 12, wherein the first area has a first thickness and the second area has a second thickness different from the first thickness, the second thickness being no greater than 100 μm, as measured according to Thickness Test.

16. The absorbent article according to claim 12, wherein the second area is located in a wall of at least one of the one or more protruded areas.

17. The absorbent article according to claim 12, wherein the second area is a highly heat-fused area.

18. The absorbent article according to claim 12, wherein the liquid permeable topsheet comprises the three dimensional nonwoven.

19. The absorbent article according to claim 12, wherein at least part of the garment-facing surface is formed by the three dimensional nonwoven.

20. A three dimensional nonwoven comprising:
   one or more protruded areas comprising a first area having a first light reflectance and a second area having a second light reflectance, and
   one or more recesses comprising a third area having a third light reflectance,
   wherein the first light reflectance is different from the second light reflectance, as measured according to Light Reflectance Test;
   wherein the difference between the first light reflectance and the second light reflectance is no less than 6, as measured according to Light Reflectance Test; and
   wherein the three-dimensional nonwoven comprises:
      at least one continuous protruded area of the one or more protruded areas surrounding a plurality of discrete recesses of the one or more recesses, or
      at least one continuous recess of the one or more recesses surrounding a plurality of discrete protruded areas of the one or more protruded areas.

21. The three dimensional nonwoven of claim 20, wherein at least one of the one or more recesses comprises a plurality of elements selected from the group of apertures, embosses, and combinations thereof.

* * * * *